United States Patent
Alterki et al.

(10) Patent No.: US 12,390,156 B1
(45) Date of Patent: Aug. 19, 2025

(54) IDENTIFICATION OF METABOLITES FOR DIAGNOSIS AND TREATMENT FOR SLEEP APNEA

(71) Applicants: Sabah Al-Ahmad Center for Giftedness and Creativity, Safat (KW); Dasman Diabetes Institute, Dasman (KW)

(72) Inventors: Abdulmohsen Alterki, Dasman (KW); Jehad Ahmed Abubaker, Dasman (KW); Mohamed Abu-Farha, Dasman (KW); Fahd Al-Mulla, Safat (KW)

(73) Assignees: Sabah Al-Ahmad Center for Giftedness and Creativity, Safat (KW); Dasman Diabetes Institute, Dasman (KW)

( * ) Notice: Subject to any disclaimer, the term of this patent is extended or adjusted under 35 U.S.C. 154(b) by 0 days.

(21) Appl. No.: 19/196,566

(22) Filed: May 1, 2025

(51) Int. Cl.
   *A61B 5/00* (2006.01)
   *G01N 33/68* (2006.01)
   *G01N 33/92* (2006.01)

(52) U.S. Cl.
   CPC .......... *A61B 5/4818* (2013.01); *A61B 5/4836* (2013.01); *G01N 33/6848* (2013.01); *G01N 33/6893* (2013.01); *G01N 33/92* (2013.01); *G01N 2570/00* (2013.01); *G01N 2800/2864* (2013.01)

(58) Field of Classification Search
   None
   See application file for complete search history.

(56) References Cited

FOREIGN PATENT DOCUMENTS

| | | |
|---|---|---|
| CN | 117747100 B | 5/2024 |
| JP | 2024134806 A | 10/2024 |

OTHER PUBLICATIONS

"Metabolomics in Sleep, Insomnia and Sleep Apnea", Publication date: Sep. 30, 2020.
"Metabolism of sleep and aging: Bridging the gap using metabolomics", Publication date: Dec. 19, 2019.

*Primary Examiner* — Xiaoyun R Xu
(74) *Attorney, Agent, or Firm* — Nath, Goldberg & Meyer; Joshua B. Goldberg

(57) ABSTRACT

The present subject matter relates to a method of diagnosing and treating sleep apnea (SA) in a subject. The method may include determining whether the subject needs a Polysomnography by obtaining a biological sample from the subject to determine if the subject has a metabolite selected from the group consisting of PC-O-(38:3), SM (43:1), LPC (24:1), PC (46:1), and TG (44:1). Expression of one of the metabolites may be associated with the presence of SA in a subject. If the subject has a metabolite associated with the presence of SA, then the method includes conducting a Polysomnography on the subject to further determine if the subject has SA. If the subject is further determined to have SA, the method may then include treating the subject with a treatment of SA selected from the group consisting of ENT multilevel surgery, continuous positive airway pressure therapy, and bariatric surgery.

13 Claims, 5 Drawing Sheets

IDENTIFICATION OF METABOLITES FOR DIAGNOSIS AND TREATMENT FOR SLEEP APNEA

1. FIELD

The present disclosure relates to a method for diagnosing and treatment of sleep apnea.

2. DESCRIPTION OF THE RELATED ART

Sleep Apnea (SA) is a prevalent condition characterized by repetitive episodes of complete or partial upper airway obstruction during sleep, leading to reduced oxygen saturation and disrupted sleep. Currently, the diagnosis of Sleep Apnea (SA) is primarily reliant on Polysomnography (PSG), which is costly and not widely accessible. Furthermore, there is a lack of reliable biomarkers to assist with the diagnosis of SA and to predict treatment response in SA patients. There is an urgent need for non-invasive, accessible biomarkers that can aid in the diagnosis of SA and predict the efficacy of various treatments, including ENT (ear, nose, and throat) multilevel surgery, continuous positive airway pressure (CPAP) therapy, and bariatric surgery.

Thus, new methods of diagnosing SA and solving the aforementioned problems are desired.

SUMMARY

The present subject matter relates to medical diagnostics and treatment, with a focus on identifying metabolites predictive of Sleep Apnea (SA). These metabolites can be used to determine the need for a sleep study and assess the effectiveness of subsequent treatments. SA affects approximately 20% of the population and is strongly linked to conditions such as diabetes, cardiovascular disease, heart dysfunction, obesity, metabolic disorders, and increased mortality risk. Most people with SA remain undiagnosed and untreated due to the limited availability of sleep labs, high costs, and inaccessibility. A simple, well-validated test capable of detecting metabolites for SA may enable mass screening, allowing proper identification of individuals who need sleep studies and appropriate treatment.

The present subject matter relates to a method of diagnosing and treating SA in a patient. The method may include determining whether the patient needs a PSG by obtaining a biological sample from the patient and performing mass spectrometry (MS) for metabolomics analyses on the biological sample to determine if the subject has an altered level of a metabolite selected from the group consisting of PC-O-(38:3), SM (43:1), LPC (24:1), PC (46:1), and TG (44:1). The presence of an altered level of one of the metabolites may be associated with the presence of SA in a patient. If the patient has an altered level of a metabolite associated with the presence of SA, then the method includes conducting a PSG on the patient to further determine if the patient has SA. If the patient is further determined to have SA, the method may then include treating the patient with a treatment of SA selected from the group consisting of ENT multilevel surgery, continuous positive airway pressure (CPAP) therapy, and bariatric surgery.

The method may further include taking an additional biological sample from the patient in a timeframe of 3 months to 6 months after the treatment of SA and detecting a new level of the metabolite. If no difference in the new level of the metabolite is detected, then the method may include administering a new treatment for SA to the patient.

These and other features of the present subject matter will become readily apparent upon further review of the following specification.

DETAILED DESCRIPTION OF THE PREFERRED EMBODIMENTS

Figure 1:
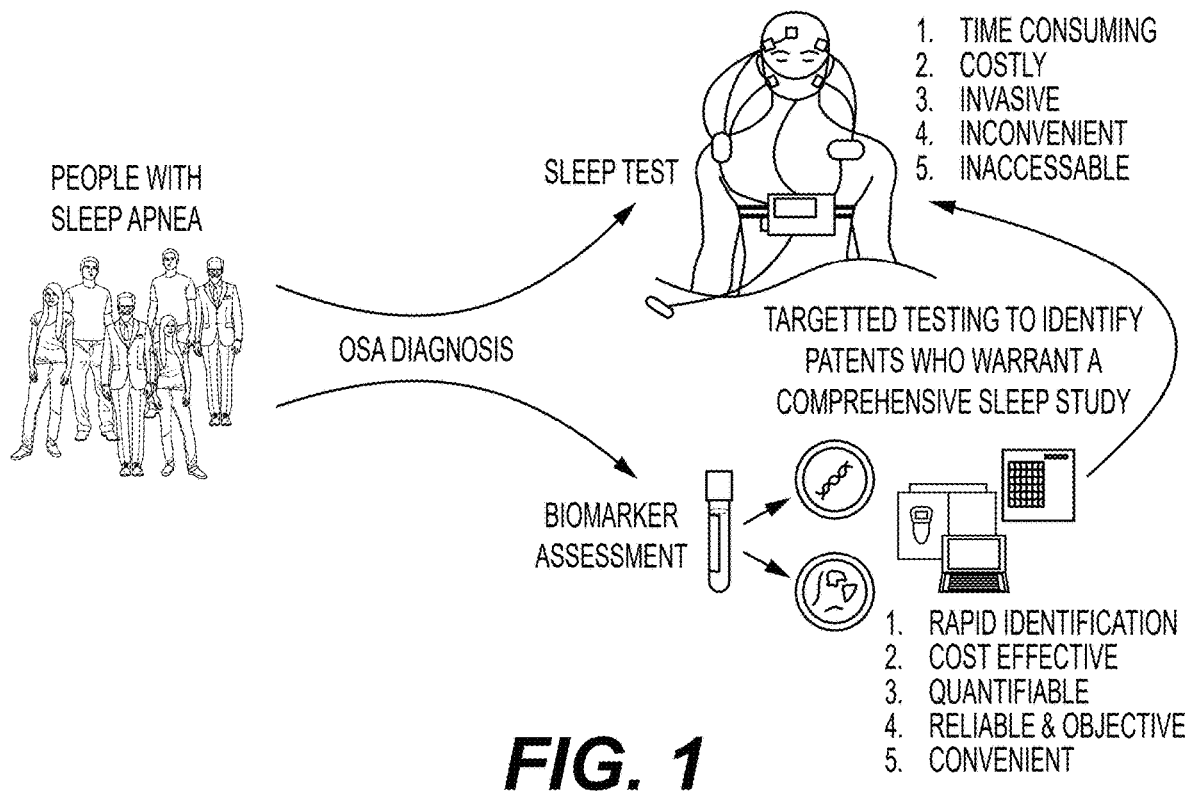
FIG. 1 depicts a diagram of biomarker screening with Sleep testing for SA diagnosis.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as sleep apnea or obstructive sleep apnea.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to medical diagnostics and treatment, with a focus on identifying metabolites predictive of Sleep Apnea (SA). These metabolites can be used to determine the need for a sleep study and assess the effectiveness of subsequent treatments. SA affects approximately 20% of the population and is strongly linked to conditions such as diabetes, cardiovascular disease, heart dysfunction, obesity, metabolic disorders, and increased mortality risk. Most people with SA remain undiagnosed and untreated due to the limited availability of sleep labs, high costs, and inaccessibility. A simple, well-validated test capable of detecting metabolites for SA would enable mass screening, allowing proper identification of individuals who need sleep studies and appropriate treatment (FIG. 1).

Furthermore, these metabolites could be tracked over time to monitor treatment efficacy and guide adjustments as needed. The method described herein may be used by all health care providers, including doctors dealing with patients diagnosed with SA, sleep disturbances, prediabetes, diabetes, cardiovascular disease, obesity, sexual and metabolic dysfunctions. In addition, biosensors and biomonitoring devices (point-of-care diagnostics) that detect any combination or all the metabolites from bodily fluids may be used directly by individuals for self-diagnosis.

The present subject matter relates to a method of diagnosing and treating SA in a subject. The method may include determining whether the subject needs a PSG by obtaining a biological sample from the subject and determining if the subject has an altered level of a metabolite selected from the group consisting of PC-O-(38:3), SM (43:1), LPC (24:1), PC (46:1), and TG (44:1). For clarity, the numbers in parentheses indicate the total carbon number and the number of double bonds for specific metabolite species. For example, SM (43:1) represents a sphingomyelin species with 43 carbons in its fatty acyl chain and 1 double bond.

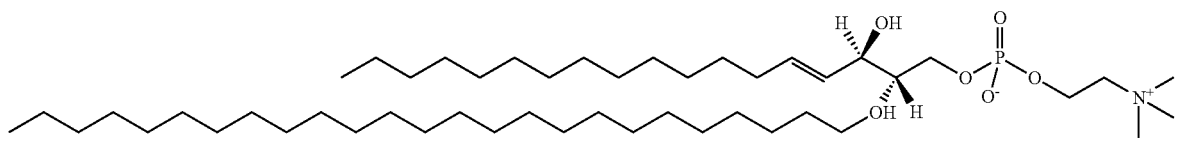 [SMILES: CCCCCCCCCCCCC/C=C/[C@@H](O)[C@H](COP(=O)([O-])OCC[N+](C)(C)C)OCCCCCCCCCCCCCCCCCCCCCCCCC]

The presence of an altered level of one of the metabolites may be associated with the presence of SA in a subject. If the subject has an altered level of a metabolite associated with the presence of SA, the method may include conducting a PSG on the subject to further determine if the subject has SA. If the subject is further determined to have SA, the method may include treating the subject with a treatment of SA selected from the group consisting of ENT multilevel surgery, continuous positive airway pressure (CPAP) therapy, and bariatric surgery.

The metabolite PC-O-(38:3) may be described as PC (16:1(9Z)/22:2(13Z,16Z)) and is a phosphatidylcholine (PC or GPCho).

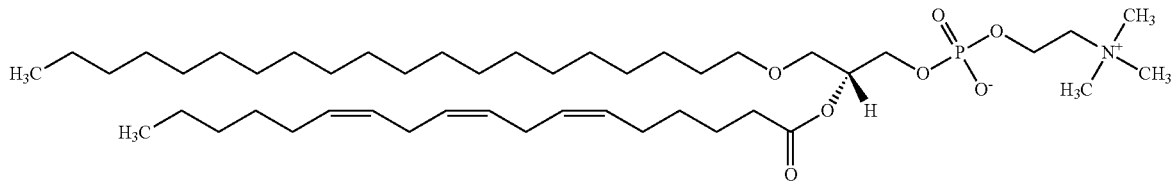 [SMILES: CCCCC/C=C\C/C=C\C/C=C\CCCCC(=O)O[C@H](COCCCCCCCCCCCCCCCCCCCC)COP(=O)([O-])OCC[N+](C)(C)C]

PC-O-(38:3) is a glycerophospholipid in which a phosphorylcholine moiety occupies a glycerol substitution site. As is the case with diacylglycerols, glycerophosphocholines may have many different combinations of fatty acids of varying lengths and saturation attached at the C-1 and C-2 positions. Fatty acids containing 16, 18 and 20 carbons are the most common. PC (16:1(9Z)/22:2(13Z,16Z)), in particular, includes one chain of palmitoleic acid at the C-1 position and one chain of docosadienoic acid at the C-2 position.

Metabolite LysoPC (24:1) is a lysophospholipid with a phosphorylcholine moiety occupying a glycerol substitution site. It is a monoglycerophospholipid with different combinations of fatty acids of varying lengths and saturation attached at the C-1 (sn-1) position.

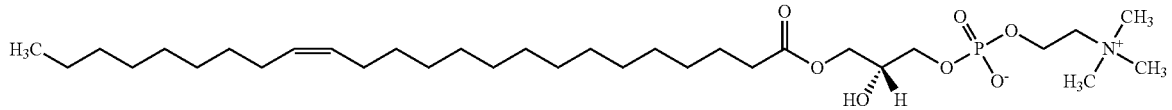 [SMILES: CCCCCCCC/C=C\CCCCCCCCCCCCCC(=O)OC[C@@H](O)COP(=O)([O-])OCC[N+](C)(C)C]

Metabolite PC (46:1) is a phospholipid that is abundant in mammalian cell membranes3.

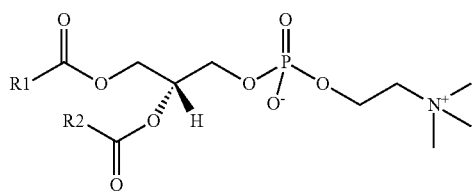

It is associated with energy metabolism and disease progression. The Metabolomics Workbench Metabolite Database contains structures and annotations of biologically relevant metabolites.

Metabolite TG (44:1) is a saturated triglyceride species that is a marker exclusively for liver fat but not visceral or pancreatic fat.

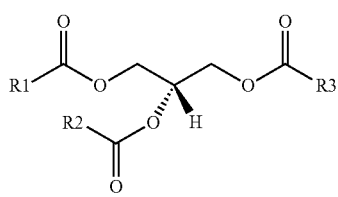

In an embodiment, the determination of the presence of an altered level of a metabolite in a subject may be based on a level of the metabolite in a group of subjects that tested positive for SA in a PSG as compared to a level of the metabolite in a group of Healthy. An alteration in the level of the metabolite present in the subject's biological sample in the same direction as previously observed in the group of subjects that tested positive for SA (either an increase or a decrease in the detected level of the metabolite) may be considered a positive indicator of SA.

In various embodiments, the biological sample may be selected from the group consisting of plasma, blood, urine, and saliva. In particular embodiments, the biological sample may be plasma.

In other embodiments, the method may further include taking an additional biological sample from the subject in a timeframe of 3 months to 6 months after the treatment of SA and detecting a new level of the metabolite associated with SA. If no difference in the new level of the metabolite is detected, then the method may include administering a new treatment for SA to the subject.

In another embodiment, the present subject matter may relate to a method of diagnosing and treating sleep apnea (SA) in a subject. The method may include obtaining a biological sample from the subject and detecting in the biological sample the presence of an altered level of a metabolite selected from the group consisting of PC-O-(38:3), SM (43:1), LPC (24:1), PC (46:1), and TG (44:1). The presence of an altered level of one of the metabolites may be associated with the presence of SA in the subject based on a level of the metabolites in subjects that tested positive for SA in a Polysomnography (PSG) as compared to the level of the metabolites in healthy subjects. If the presence of the altered level of the metabolite is detected in the subject at a level associated with SA, then the method may include treating the subject with a treatment of SA selected from the group consisting of ENT multilevel surgery, continuous positive airway pressure (CPAP) therapy, and bariatric surgery.

In various embodiments, the biological sample may be selected from the group consisting of plasma, blood, urine, and saliva. In particular embodiments, the biological sample is plasma.

In some embodiments, the method may further include taking an additional biological sample from the subject in a timeframe of 3 months to 6 months after the treatment of SA and detecting a new level of the metabolites. If no difference in the new level of the metabolites is detected, then a new treatment may be administered to the subject.

In other embodiments, the biological sample may be tested using mass spectrometry (MS) for metabolomics analyses. Testing for levels of various metabolites may also be performed using any means now known or developed in the future to detect metabolites.

In still other embodiments, the treatment of SA used may be based on the metabolite detected.

EXAMPLES

Mass spectrometry (MS) for metabolomics analyses was used for testing the samples for the intended metabolites, specifically the Q-Exactive HF LC-ESI-MS/MS system from Thermo Fisher Scientific.

Metabolites were extracted from plasma samples collected from SA patients before and after intervention, as well as from healthy controls. The extracted metabolites were further purified and quantified using mass spectrometry for metabolic profiling analyses. Metabolites that were differentially expressed and associated with SA were selected for further analysis to validate their diagnostic potential.

The levels of metabolites across samples were evaluated and correlated with various SA indices, such as an apnea index (AI) and the apnea-hypopnea index (AHI), obtained through polysomnography, to confirm their comparable diagnostic potential.

Figure 2A:
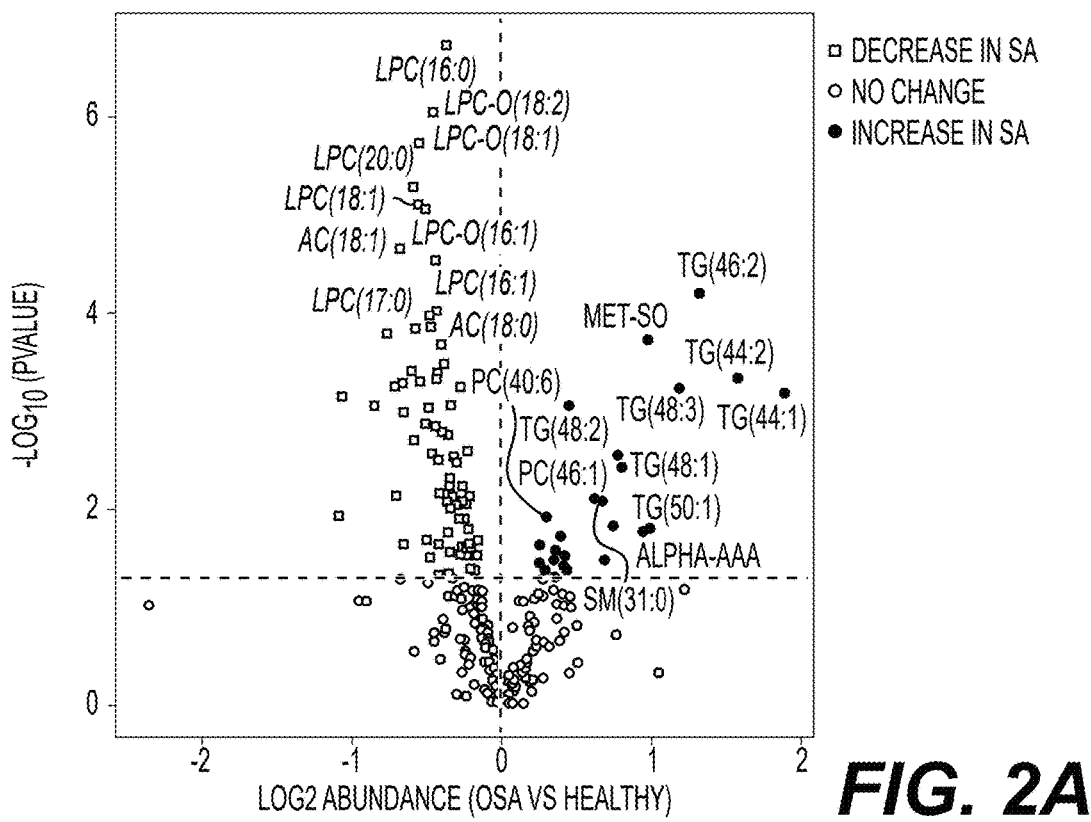
FIG. 2A is a graph showing metabolites found in a control group compared with individuals diagnosed with SA.
Figure 2B:
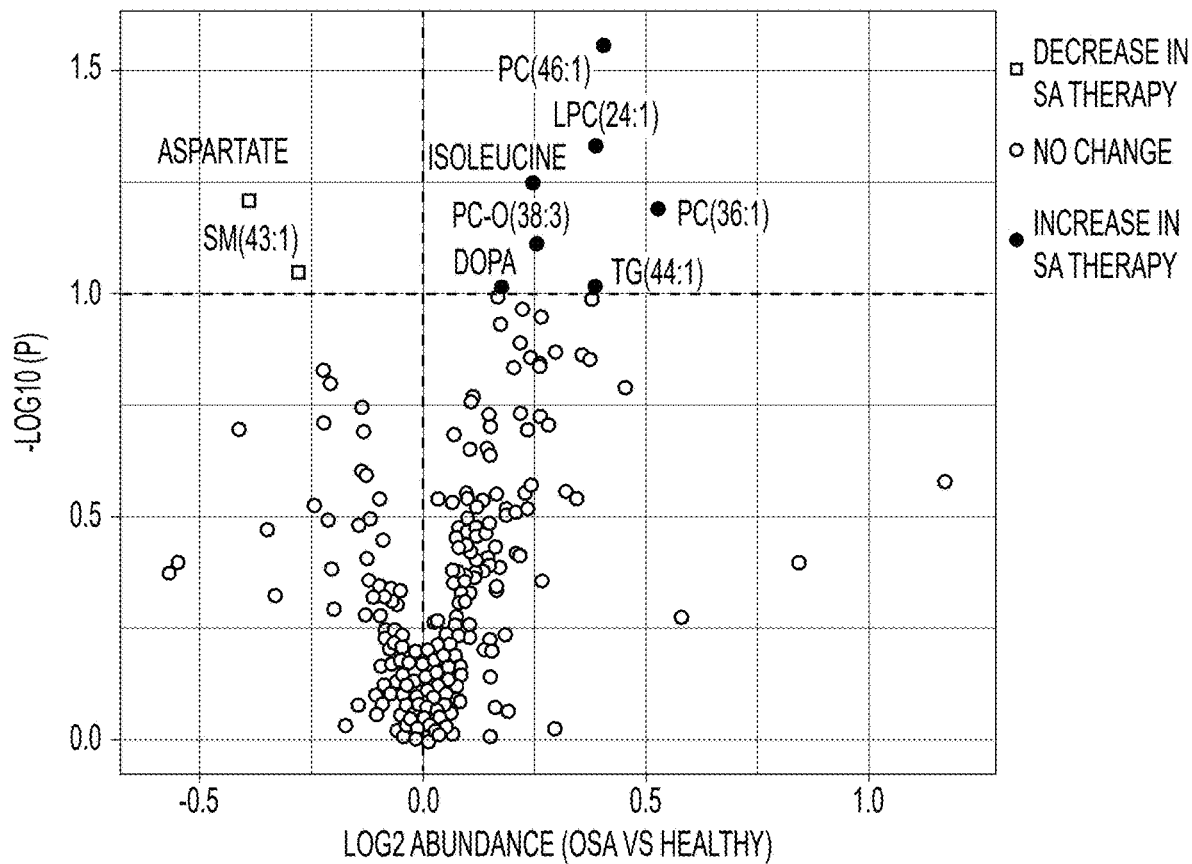
FIG. 2B is a graph showing metabolites found in patients having undergone therapy for SA compared with individuals diagnosed with SA.

The levels of metabolites were measured in both SA patients and healthy controls at the time of diagnosis (FIG. 2A), and their diagnostic potential was compared to polysomnography, the gold standard methods for sleep apnea diagnosis. Additionally, these molecules were evaluated in SA patients after 3-6 months of intervention to assess their response to treatment (FIG. 2B).

Figure 2C:
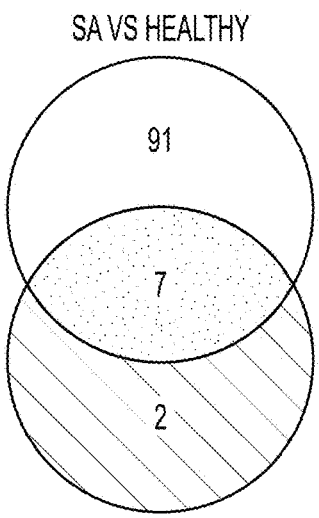
FIG. 2C is a Venn-diagram showing the overlap of metabolites found in SA diagnosis vs Healthy Individuals and SA therapy with SA diagnosis.
Figure 2D:
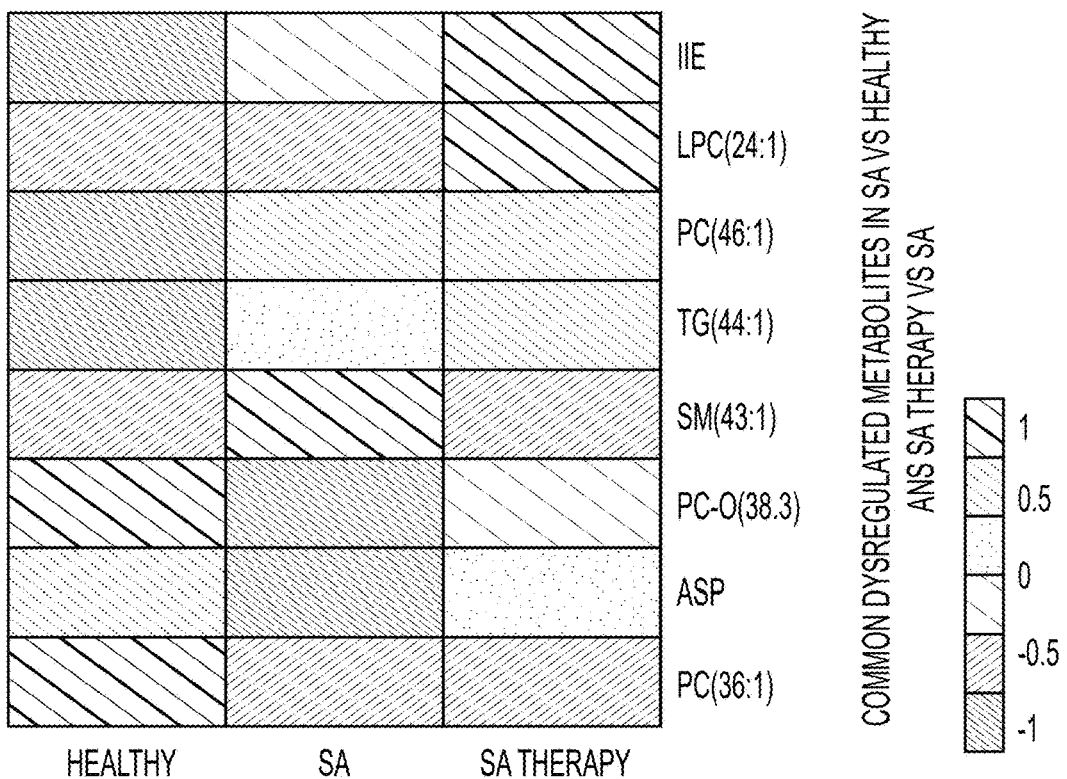
FIG. 2D shows the levels of metabolites in healthy individuals, individuals diagnosed with SA and individuals that have undergone SA therapy.
Figure 3A:
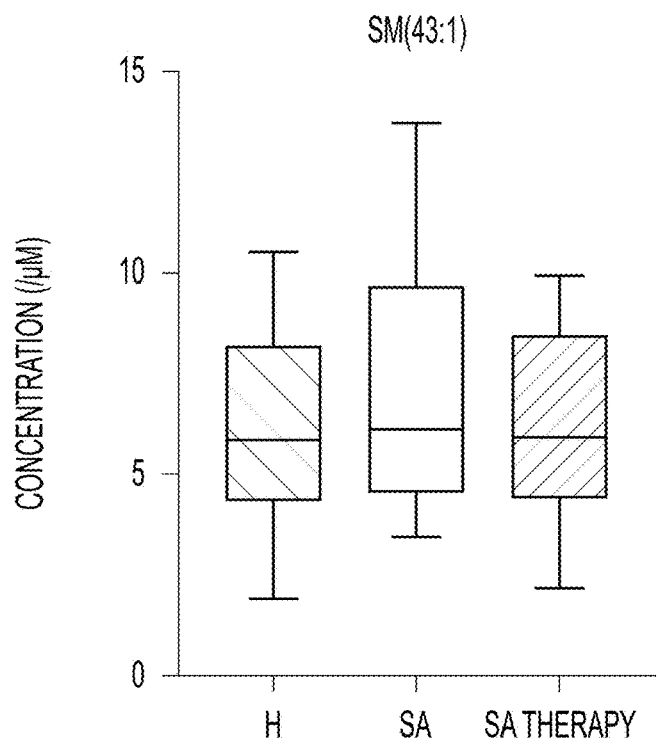
FIG. 3A is a graph showing levels of the SM (43:1) metabolite in a Healthy group (H), individuals diagnosed with SA, and individuals having undergone SA therapy.
Figure 3B:
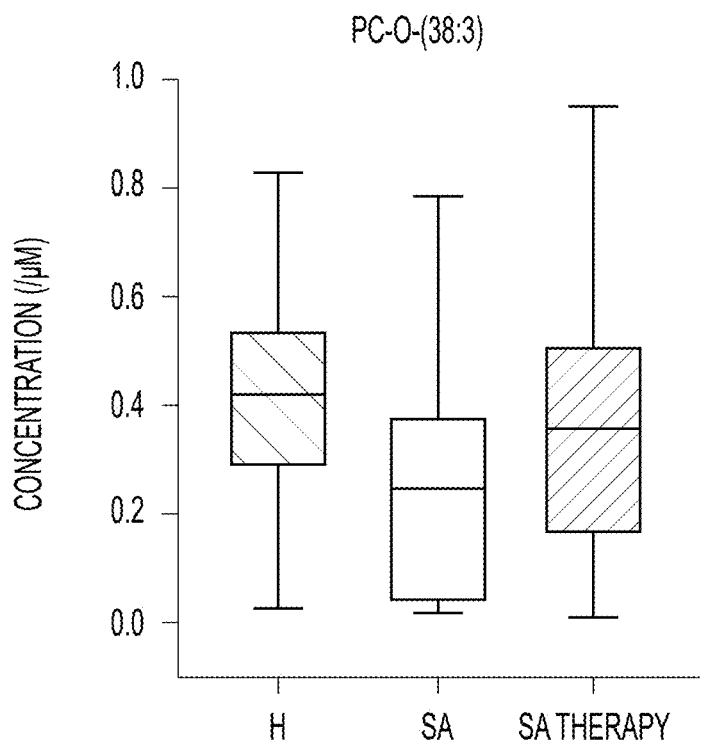
FIG. 3B is a graph showing levels of the PC-O-(38:3) in a Healthy group (H), individuals diagnosed with SA, and individuals having undergone SA therapy.
Figure 3C:
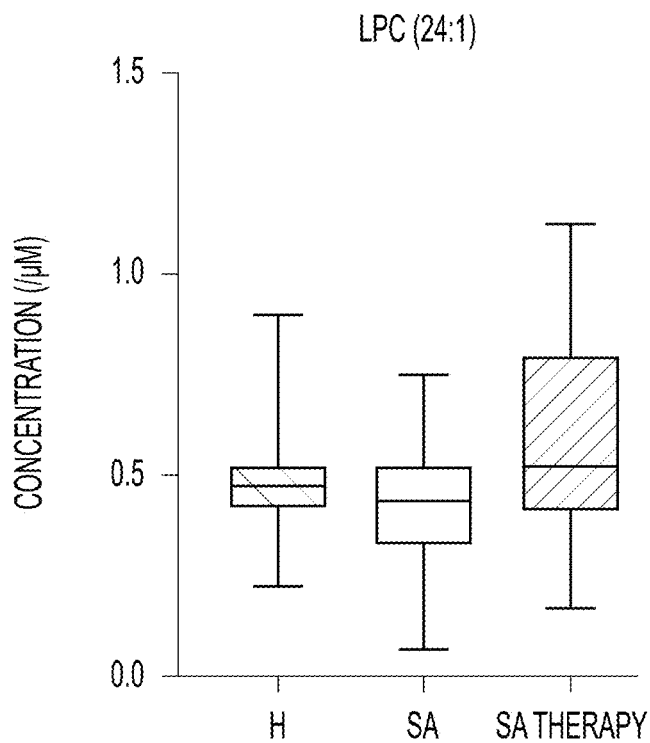
FIG. 3C is a graph showing levels of the LPC (24:1) in a Healthy group (H), individuals diagnosed with SA, and individuals having undergone SA therapy.
Figure 3D:
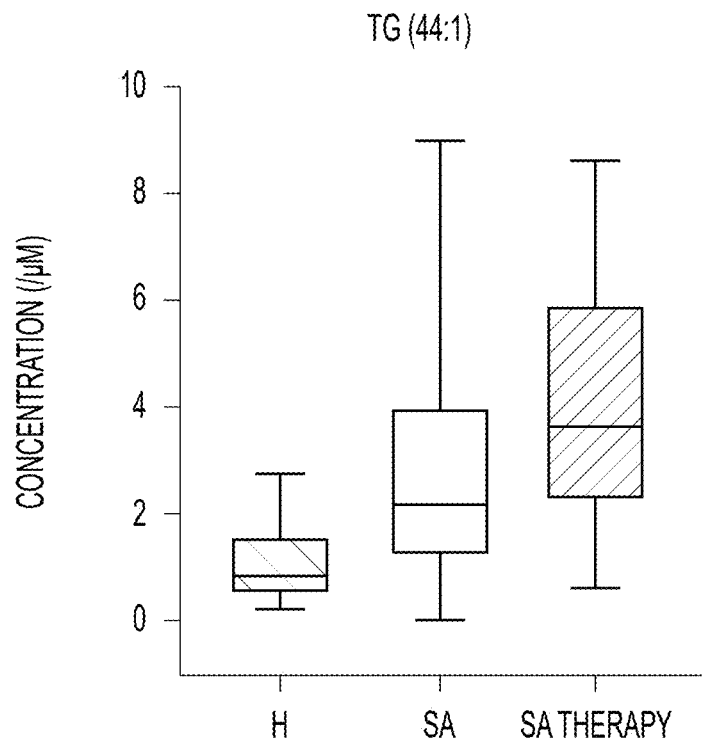
FIG. 3D is a graph showing levels of the TG (44:1) metabolite in a Healthy group (H), individuals diagnosed with SA, and individuals having undergone SA therapy.
Figure 3E:
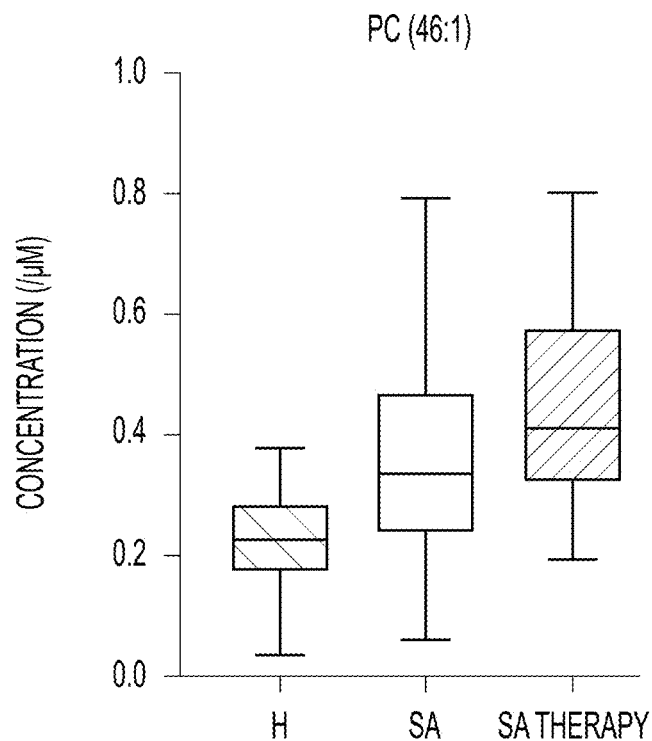
FIG. 3E is a graph showing levels of the PC (46:1) metabolite in a Healthy group (H), individuals diagnosed with SA, and individuals having undergone SA therapy.

FIG. 2C is a Venn-diagram showing the overlap of seven metabolites between patients diagnosed with SA and healthy individuals compared with patients that have undergone therapy for SA and patients diagnosed with SA. The data is also shown in Table 1. Finally, the level of expression of the metabolites in each of the three groups, healthy, SA, and SA therapy, is shown in FIG. 2D.

TABLE 1

| Metabolite | SA v Healthy | | SA therapy vs SA | |
| --- | --- | --- | --- | --- |
| | log2(FC) | p-value | log2(FC) | p-value |
| Asp | −0.35 | 0.03 | 0.38 | 0.03 |
| PC-O-(38:1) | 0.24 | 0.04 | 0.35 | 0.01 |
| Ile | −0.04 | 0.21 | 0.25 | 0.03 |
| LPC (24:1) | −0.30 | 0.39 | 0.99 | 0.02 |
| PC (46:1) | 0.62 | 0.004 | 0.41 | 0.01 |
| SM (43:1) | 0.41 | 0.04 | −0.28 | 0.05 |
| TG (44:1) | 1.88 | 0.003 | 0.39 | 0.05 |

The treatment response was assessed after a minimum follow-up period of 3 months post-intervention, with an average follow-up duration of 5 months. This timeframe is generally sufficient, based on earlier reports, to observe the necessary changes or improvements resulting from therapy.

The levels of these markers were compared to various sleep indices, such as sleep oxygenation, AI, and AHI scores, obtained through polysomnography conducted in a sleep laboratory. Strong and significant correlations were observed between the markers and the AI and AHI readings, supporting their diagnostic and predictive potential for identifying SA.

It is to be understood that the method of diagnosing and treating SA described are not limited to the descriptions herein, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of diagnosing and treating sleep apnea (SA) in a subject, the method comprising:
    determining whether the subject needs a Polysomnography by:
        obtaining a biological sample from the subject;
        performing or having performed on the biological sample mass spectrometry for proteomics and metabolomics analyses to determine if the subject has an altered level of a metabolite selected from the group consisting of PC-O-(38:3), SM (43:1), LPC (24:1), PC (46:1), and TG (44:1), wherein the presence of an altered level of at least one of the metabolites is associated with the presence of SA in a subject;
        conducting a Polysomnography on the subject to further determine if the subject has SA; and
        treating the subject with a treatment of SA selected from the group consisting of ENT multilevel surgery, continuous positive airway pressure (CPAP) therapy, and bariatric surgery.

2. The method of claim 1, wherein the altered level of the metabolite in the subject is based on a level of the metabolite detected in a group of subjects that tested positive for SA in a Polysomnography as compared to a level of the metabolite detected in a group of healthy subjects.

3. The method of claim 1, wherein the biological sample is selected from the group consisting of plasma, blood, urine, and saliva.

4. The method of claim 3, wherein the biological sample is plasma.

5. The method of claim 1, further comprising taking an additional biological sample from the subject in a timeframe comprising 3 months to 6 months after the treatment of SA and detecting a new level of the metabolite.

6. The method of claim 5, further comprising administering a new treatment for SA to the subject.

7. A method of diagnosing and treating sleep apnea (SA) in a subject, the method comprising:
    obtaining a biological sample from the subject;
    detecting in the biological sample the presence of an altered level of a metabolite selected from the group consisting of PC-O-(38:3), SM (43:1), LPC (24:1), PC (46:1), and TG (44:1), wherein the presence of an altered level of one or more of the metabolites is associated with the presence of SA in a subject based on a level of the metabolites detected in a group of subjects that tested positive for SA in a Polysomnography (PSG) as compared to a level of the metabolites detected in a group of healthy subjects;
    treating the subject with a treatment of SA selected from the group consisting of ENT multilevel surgery, continuous positive airway pressure (CPAP) therapy, and bariatric surgery.

8. The method of claim 7, wherein the biological sample is selected from the group consisting of plasma, blood, urine, and saliva.

9. The method of claim 8, wherein the biological sample is plasma.

10. The method of claim 7, further comprising taking an additional biological sample from the subject in a timeframe comprising 3 months to 6 months after the treatment of SA and detecting a new level of the metabolite.

11. The method of claim 10, wherein if no difference in the new level of the metabolite is detected, then administered to the subject a new treatment.

12. The method of claim 7, wherein the biological sample is tested using mass spectrometry (MS) for metabolomics analyses.

13. The method of claim 7, wherein the treatment of SA used is based on the metabolite detected.

* * * * *